United States Patent [19]
Garber et al.

[11] Patent Number: 6,156,727
[45] Date of Patent: Dec. 5, 2000

[54] ANTI-ATHEROSCLEROTIC PEPTIDES AND A TRANSGENIC MOUSE MODEL OF ANTHEROSCLEROSIS

[75] Inventors: David W. Garber; Gattadahalli M. Anantharamaiah, both of Birmingham, Ala.

[73] Assignee: UAB Research Foundation, Birmingham, Ala.

[21] Appl. No.: 08/924,280

[22] Filed: Sep. 5, 1997

Related U.S. Application Data

[60] Provisional application No. 60/025,505, Sep. 5, 1996.
[51] Int. Cl.⁷ .............................. A61K 38/00; C07K 5/00
[52] U.S. Cl. .............................................. 514/12; 530/324
[58] Field of Search ................................ 530/350; 514/12

[56] References Cited

U.S. PATENT DOCUMENTS 4,643,988  2/1987  Segrest et al. ............................ 514/12

OTHER PUBLICATIONS

Tytler et al. Synthetic peptides in the study of viral fusion, inflammation, and athersclerosis. In: Peptides: design, synthesis, and biological activity. Basava and Anantharamaiah, editors, p. 113–132, 1994.

*Primary Examiner*—Karen Cochrane Carlson
*Assistant Examiner*—Davesh Srivastava
*Attorney, Agent, or Firm*—Benjamin Aaron Adler

[57] ABSTRACT

The present invention provides an anti-atherosclerotic peptide, said peptide being an amphipathic helical peptide compared with human apoA-I, characterized by having at least 4 of the following 8 properties: a tandem repeating class A amphipathic helix linked by a proline which forms an optimal arrangement for lipid association, has bilayer membrane stabilizing properties, stimulates HIV-I Gp41-induced cell fusion, stimulates neutrophil activation, stimulates BSA-induced lysis of fatty acid-containing vesicles, stimulates human placental lactogen synthesis, effluxes phospholipid and cellular cholesterol from cholesterol-loaded cells, and competes with HDL for binding to cells. The present invention is also directed to pharmaceutical compositions, transgenic animals expressing a protein disclosed herein, vectors expressing such proteins.

4 Claims, 19 Drawing Sheets

(14 of 19 Drawing Sheet(s) Filed in Color)

1 2 3 4 5 6

```
                           SEQUENCE LISTING (1) GENERAL INFORMATION:

(iii) NUMBER OF SEQUENCES:  9

(2) INFORMATION FOR SEQ ID NO:1:

(i) SEQUENCE CHARACTERISTICS:
             (A) LENGTH:  37 amino acids
             (B) TYPE:  amino acid
             (C) STRANDEDNESS:
             (D) TOPOLOGY:  linear (ii) MOLECULE TYPE:
             (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:  1:

Asp Trp Leu Lys Ala Phe Tyr Asp Lys Val Ala Glu Lys Leu Lys
                   5                  10                  15

Glu Ala Phe Pro Asp Trp Leu Lys Ala Phe Tyr Asp Lys Val Ala
                  20                  25                  30

Glu Lys Leu Lys Glu Ala Phe
                  35

(2) INFORMATION FOR SEQ ID NO:2:

(i) SEQUENCE CHARACTERISTICS:
             (A) LENGTH:  18 amino acids
             (B) TYPE:  amino acid
             (C) STRANDEDNESS:
             (D) TOPOLOGY: linear (ii) MOLECULE TYPE:
             (A) DESCRIPTION:  no
```

-continued (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:  2:

Asp Trp Leu Lys Ala Phe Tyr Asp Lys Val Phe Glu Lys Phe Lys
                 5                  10                  15

Glu Phe Phe (2) INFORMATION FOR SEQ ID NO:3:

(i) SEQUENCE CHARACTERISTICS:
            (A) LENGTH:  40 amino acids
            (B) TYPE:  amino acid
            (C) STRANDEDNESS:
            (D) TOPOLOGY:  linear (ii) MOLECULE TYPE:
            (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:  3:

Asp Glu Pro Asp Trp Leu Lys Ala Phe Tyr Asp Lys Val Ala Glu
                 5                  10                  15

Lys Leu Lys Glu Ala Phe Pro Asp Trp Leu Lys Ala Phe Tyr Asp
                20                  25                  30

Lys Val Ala Glu Lys Leu Lys Glu Ala Phe
                35                  40

(2) INFORMATION FOR SEQ ID NO:4:

(i) SEQUENCE CHARACTERISTICS:
            (A) LENGTH:  26 bp
            (B) TYPE:  nucleic acid
            (C) STRANDEDNESS:  single-stranded
            (D) TOPOLOGY:  linear (ii) MOLECULE TYPE:
            (A) DESCRIPTION:  other nucleic acid (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 4:

TTCAGGATGA AAGCAGCGGT GTTAAC                                                  26

(2) INFORMATION FOR SEQ ID NO:5:

(i) SEQUENCE CHARACTERISTICS:
                (A) LENGTH: 20 bp
                (B) TYPE: nucleic acid
                (C) STRANDEDNESS: single-stranded
                (D) TOPOLOGY: linear (ii) MOLECULE TYPE:
                (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 5:

TCAGAATGCT TCTTTTAGTT                                                         20

(2) INFORMATION FOR SEQ ID NO:6:

(i) SEQUENCE CHARACTERISTICS:
                (A) LENGTH: 108 bp
                (B) TYPE: nucleic acid
                (C) STRANDEDNESS: single-stranded
                (D) TOPOLOGY: linear (ii) MOLECULE TYPE:
                (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 6:

ATGAAAGCAG CGGTGTAAAC ACTAGCAGTA CTCTTCCTGA CGGGGAGTCA AGCTCGGCAT             60

```
TTCTGGCAGC AAGATGAACC CGACTGGCTG AAGGCGTTCT ACGACAAG                108
```

(2) INFORMATION FOR SEQ ID NO:7:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 7:

```
Met Lys Ala Ala Val Leu Thr Leu Ala Val Leu Phe Leu Thr Gly
            5                  10                  15

Ser Gln Ala Arg His Phe Trp Gln Gln Asp Glu Pro Asp Trp Leu
            20                  25                  30

Lys Ala Phe Tyr Asp Val
            35
```

(2) INFORMATION FOR SEQ ID NO:8:

(i) SEQUENCE CHARACTERISTICS:
        (A) LENGTH: 108 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 8:

```
GACTTCCGCA AGATGCTGTT CCACCGCCTC TTCGACTTCC TCCGCAAGGG GCTAACCAAT         60
TTTCGTAAAA TACTATTTCA TCGTCTTTTT GATTTTCTTC GTAAGACT                    108
```

(2) INFORMATION FOR SEQ ID NO:9:

-continued

```
    (i) SEQUENCE CHARACTERISTICS:
         (A) LENGTH:  35 amino acids
         (B) TYPE:   amino acid
         (C) STRANDEDNESS:
         (D) TOPOLOGY:  linear (ii) MOLECULE TYPE:
         (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:  9:

Leu Lys Ala Phe Tyr Asp Lys Val Ala Glu Lys Leu Lys Glu Ala
                 5                  10                  15

Phe Pro Asp Trp Leu Lys Ala Phe Tyr Asp Lys Val Ala Glu Lys
                20                  25                  30

Leu Lys Glu Ala Phe
                35
```

ANTI-ATHEROSCLEROTIC PEPTIDES AND A TRANSGENIC MOUSE MODEL OF ANTHEROSCLEROSIS

This application claims the benefit of U.S. Provisional application Ser. No. 60/025,505, filed Sep. 5, 1996 (MPEP §1302.04).

BACKGROUND OF THE INVENTION

1. Field of the Invention

The present invention relates generally to the fields of molecular biology, cardiovascular medicine and transgenic animals. More specifically, the present invention relates to a novel transgenic mouse model of atherosclerosis.

2. Description of the Related Art

Although atherogenesis involves many different events, abnormal accumulation of cholesterol in the artery wall has long been considered an essential element of the atherogenic process. Cholesterol deposits in the atherosclerosclerotic plaque represent both intracellular lipid deposits (foam cells) and extracellular lipid particles. The foam cells are caused by the abnormal uptake of certain lipoprotein species in circulating blood by macrophages. The origins of extracellular lipid particles are either infiltered plasma lipoproteins or cellular necrotic products.

Several reports indicate that human atherosclerosis may be a reversible process (1). Regression of experimentally induced atherosclerosis in experimental animals has been reported following dietary manipulation (2) or by the administration of hypolipedemic agents (2). Prospective epidemiological studies indicate that a strong positive correlation exists between plasma levels of LDL and VLDL. VLDL and LDL components have also been identified in human atherosclerotic plaques. However, normalipedemic patients also develop premature coronary artery disease. It has been suggested that elevated levels of HDL inhibits the development of atherosclerosis by acting as a sink for cholesterol from foam cell membranes.

It has been postulated that cholesterol lowering stabilizes atherosclerotic plaques, particularly those with eccentric, lipid-rich cores. Lesions with lipid-rich cores are particularly susceptible to intravascular hemorrhage, and are usually associated with clinical events. Foam cells are often found at the sites of plaque rupture, suggesting that plaque erosion by foam cells may be a major mechanism in predisposing atherosclerosis (12). A reduction in lipid content may alter the structure of these plaques in such a way that they are less vulnerable to rupture and other complications. This theory is in agreement with the concept of reverse cholesterol transport. In this theory, high levels of HDL are thought to promote cholesterol efflux from cells. It is therefore possible that, while reduced levels of LDL inhibit further lipid accumulation in lesions, increasing levels of HDL by 1% decreases coronary artery disease mortality by three percent.

Lipoproteins are macromolecular assemblies of specific apolipoproteins and lipids. The lipids are associated with protein components by noncovalent forces. All of the lipoproteins have cores of triglycerides and cholesteryl esters with the surface stabilized by phospholipids, cholesterol and apolipoproteins. There are some HDL particles that are devoid of core. These are discoidal and nascent particles and the newly classified preβHDL particles. During the hydrolysis of chylomicrons and VLDL some surface remnants are formed which are vesicular and these vesicular substances are associated with exchangeable apolipoproteins.

High Density Lipoproteins

Recent studies provide a strong support for the role of plasma lipoproteins in atherosclerotic plaque formation. Plaque stabilization due to rapid removal of cholesterol from macrophage-derived foam cells has been suggested to explain the rapid cessation of clinical coronary artery disease events. Epidemiological studies show an inverse correlation of HDL and apo A-I to atherosclerosis.

The inverse relationship between atherosclerosis and HDL has been well established. One prominent role of HDL appears to be that HDL is involved in the reverse-cholesterol transport, i.e., the transportation of cholesterol from peripheral tissue to the liver (3). HDL may have other beneficial roles. HDL, by regulating the inflammatory response, may also regulate the tissue injury seen in inflammatory disorders. HDL decreases antibody production and inhibits lymphocyte cellular cytotoxicity. There is a pool of apoA-I free from HDL which has been shown to effectively efflux cellular cholesterol.

Recently, it has been shown that HDL delivers cholesterol to the cells through the class B scavenger receptor SRBI. This receptor binds HDL with high affinity, and is primarily expressed in the liver and nonplacental steroidogenic tissues. Thus, HDL metabolism is distinct from LDL metabolism in which cholesterol alone is taken up by the cells and not apoA-I.

Low Density Lipoproteins

High levels of LDL are the main cause of hypercholesterolemia. LDL are enriched with free cholesterol. Due to its size (21 to 25 nm), LDL can be filtered into the arterial wall where they can initiate the atherogenic process. LDL is derived from the catabolism of VLDL. This indicates that any alteration of VLDL catabolism should alter the production of LDL. The precise mechanism whereby VLDL remnants are converted to LDL is not known.

LDL is cleared via the LDL receptor. During this process, the entire LDL particle is endocytosed, the protein apoB is proteolyzed and the cholesterol is taken up by the cells. There are other nonreceptor-dependent pathways whereby LDL is removed. Accumulating evidence indicates that oxidized LDL is atherogenic. In vitro evidence suggests that HDL is an antioxidant and prevents self-aggregation. These latter effects are thought to be directly related to the apoA-I component present in HDL.

Very Low Density Lipoproteins

Very Low Density lipoproteins are also called the Triglycerides (TG)-rich lipoproteins. Triglycerides in VLDL are hydrolyzed by the action of lipoprotein lipase (LPL). ApoC-II, an activator of LPL is present on the surface of VLDL. This hydrolysis produces surface-remnants enriched with phospholipids and core remnants. The smaller core remnants are ultimately converted to LDL. The exchangeable apolipoproteins present on the surface of VLDL are responsible for the function of VLDL. In LDL-receptor deficient mice fed a high fat diet, overexpression of LPL inhibited diet-induced atherosclerosis. Thus, increased catabolism of VLDL can inhibit atherosclerosis despite the fact the cholesterol is not metabolized via the VLDL.

Exchangeable Apolipoproteins

One of the main functions of exchangeable apolipoproteins appears to be to solubilize otherwise insoluble lipids in circulating plasma. The mechanism by which the exchangeable apolipoproteins associate with phospholipids was first proposed by Segrest et al. This group of proteins interacts with lipids through specialized helical domains (the "amphipathic helical domain". There is experimental evidence that the amphipathic helical domains are also important for functional properties of lipoproteins. ApoA-I is the major activator of the plasma enzyme LCAT that converts free cholesterol into cholesteryl ester. ApoA-I is also capable of effluxing cholesterol from cholesterol loaded cells. This may have a direct implication on the ability of HDL and apoA-I to inhibit atherosclerosis. In addition, ApoE, the protein component of VLDL, is involved in the receptor-mediated removal of VLDL.

Animal Models for Atherosclerosis

The genetically inbred mouse has been useful in deciphering the impact of a specific gene products on the lipoprotein metabolism. Currently, murine models of atherosclerosis have been used entensively for the study of atherogenic lipoproteins. However, there exists a large variation in the susceptibility of diet-induced atherosclerosis across the strains. C57BL/6 mice, the most susceptible strain, shows the largest reduction of HDL cholesterol with high fat diet administration. This implies that HDL is the major determinant of atherogenicity.

Mice overexpressing human apoA-I are resistant to diet-induced atherosclerosis. Mice overexpressing apoA-II or CETP developed severe diet-administered atherosclerosis. Moreover, mice lacking apoE develop atherosclerosis spontaneously, even without high fat diet administration. Similarly, LDL receptor gene knockout mice also develop atherosclerosis and are considered to be models of familial hypercholesterolemia. These produce severe atherosclerosis when fed with a high fat diet.

Other animal models, such as rabbits, can be used for studying the role of apolipoproteins in atherosclerosis. However, it is difficult to genetically breed to produce transgenes in other animals. Another drawback in the transgenic mouse models of the prior art is due to the size of the animals, it is difficult to obtain several samples of plasma during a study to measure changes in lipoprotein profiles that occur during an experiment.

The prior art is deficient in the lack of a novel transgenic mouse model of atherosclerosis. The present invention fulfills this longstanding need and desire in the art.

SUMMARY OF THE INVENTION

Recent developments provide strong support for the role of plasma lipoproteins in atherosclerotic plaque formation. Plaque stabilization due to rapid removal of cholesterol from macrophage-derived foam cells has been suggested to explain the rapid cessation of clinical coronary artery disease events after aggressive lipid-modifying therapy (1). Transgenic mice studies using over expression and gene knockout of apolipoproteins A-I and E suggest that remnant lipoproteins are atherogenic (2,3).

By employing transgenic technology, a mouse strain that is typically susceptible to diet-induced atherosclerosis was made to express high amounts of human apolipoproteinA-I and HDL (4, 5). Compared to control animals, the mice expressing the human transgene were found to be significantly protected from the development of fatty streak lesions. Thus, human apoA-I can inhibit the development of atherosclerosis. Interventional animal experiments have shown that administration of HDL not only inhibited the development but also reduced the progression of atherosclerotic lesions in rabbits (6,7).

In one embodiment of the present invention, there is a novel synthetic peptide having the sequence shown in SEQ No. 1 below, that is capable of inhibiting atherosclerosis.

In another embodiment of the present invention, there is provided a pharmaceutical composition, comprising a novel synthetic peptide having the sequence shown in SEQ No. 2 below and a pharmaceutically acceptable carrier. This sequence can be expressed in vivo.

In yet another embodiment of the present invention, there is provided a novel synthetic peptide having the sequence shown in SEQ No. 3 below.

In another embodiment of the present invention, there is provided a pharmaceutical composition, comprising a novel synthetic peptide having the sequence shown in SEQ No. 3 below and a pharmaceutically acceptable carrier.

In yet another embodiment of the present invention, there is provided a transgenic animal expressing one of the proteins shown in SEQ Nos. 1–3.

In still yet another embodiment of the present invention, there is provided a vector expressing one of the proteins shown in SEQ Nos. 1–3.

In still yet another embodiment of the present invention, there is provided a host cell transfected with a vector expressing one of the proteins shown in SEQ Nos. 1–3.

In still yet another embodiment of the present invention, there is provided a method of treating atherosclerosis in an animal in need of such treatment comprising the step of administering to the animal a pharmacologically effective dose of a antiatherosclerotic peptide shown in SEQ Nos. 1–3.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the effects of intraperitoneal administration over 16 weeks of peptide 18A-Pro-18A to high fat diet administered C57BL 6/J mice showing cross sections from the aorta.

FIG. 2 shows the histology of aortal cross sections from in vitro fertilized animals and shows lesions of different severity for different animals.

DETAILED DESCRIPTION OF THE INVENTION

Figure 1A:
FIG. 1A shows the saline administered mouse and extensive foam cells can be seen.
Figure 1B:
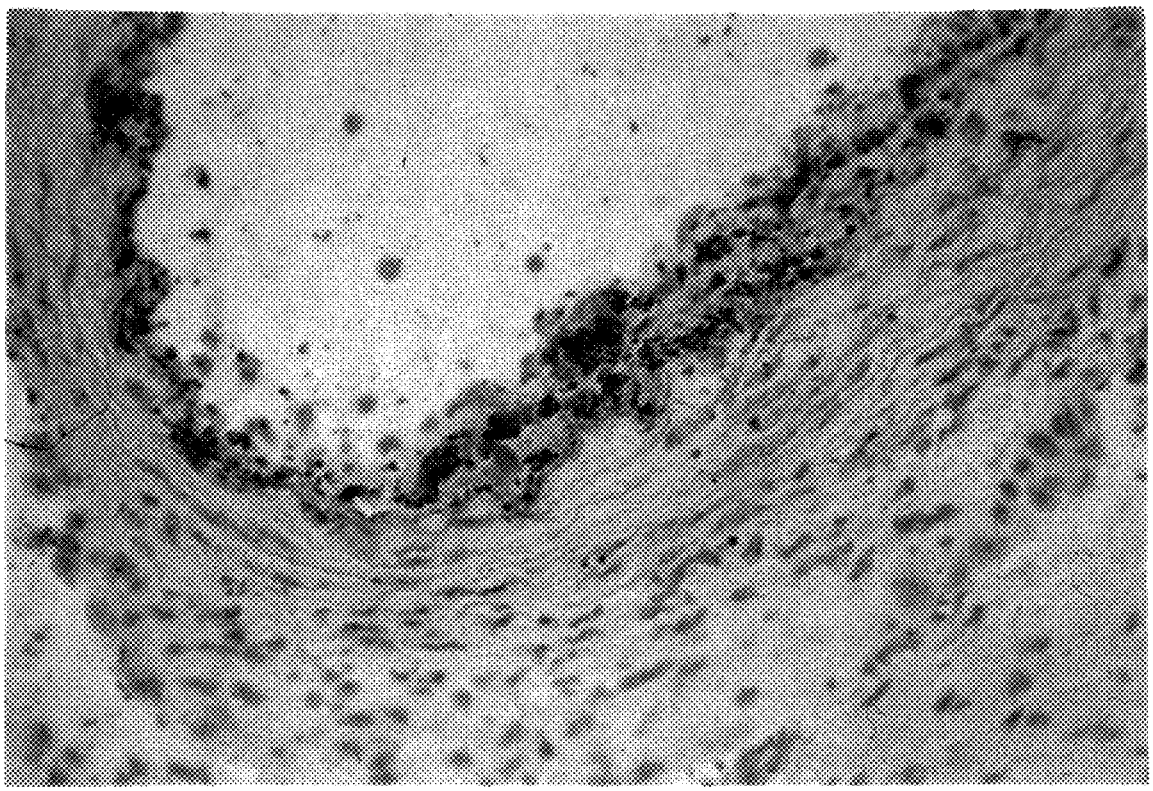
FIG. 1B shows an expanded view of the region of FIG. 1A.
Figure 1C:
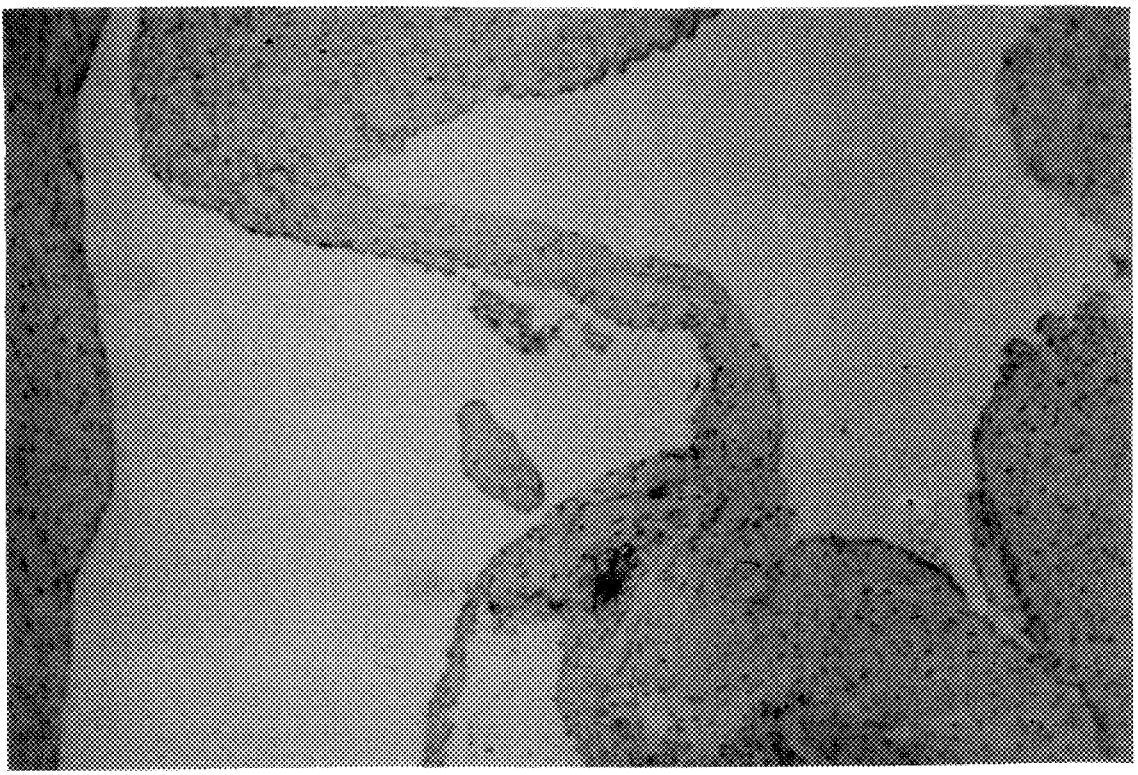
FIG. 1C shows a peptide administered mouse. Although lipid granules can be observed, no foam cells can be seen.
Figure 1D:
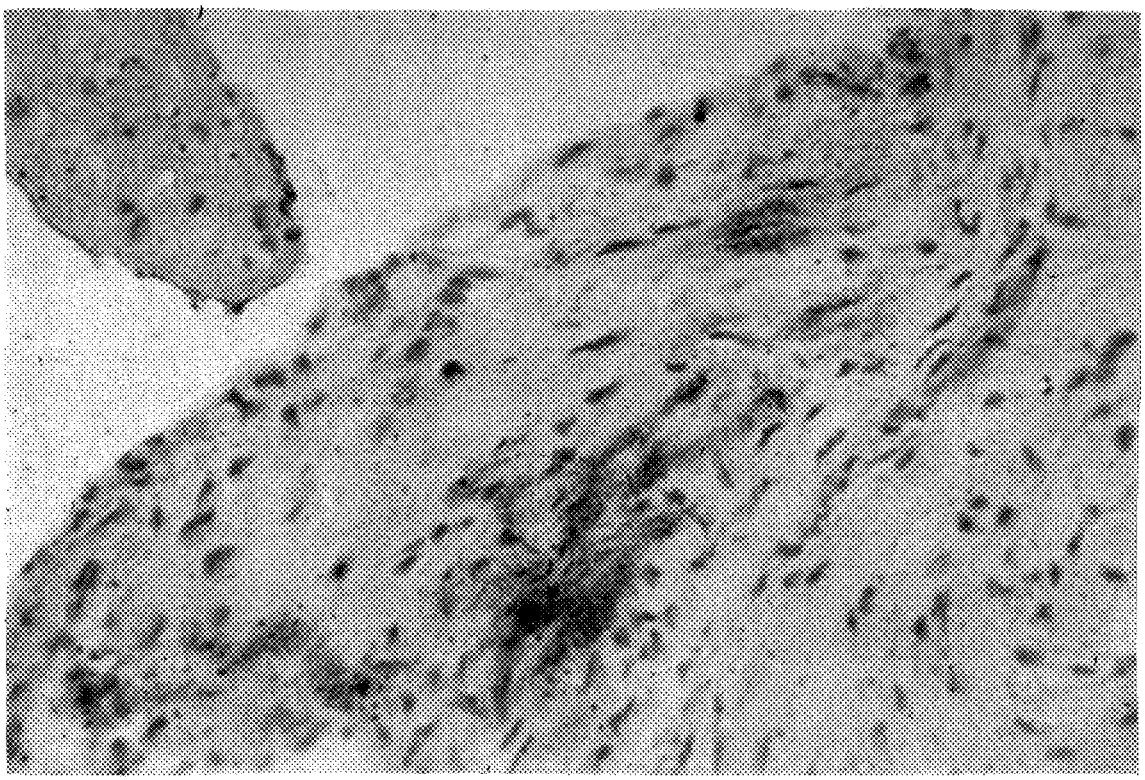
FIG. 1D shows an expanded view of the region shown in FIG. 1C.
Figure 1E:
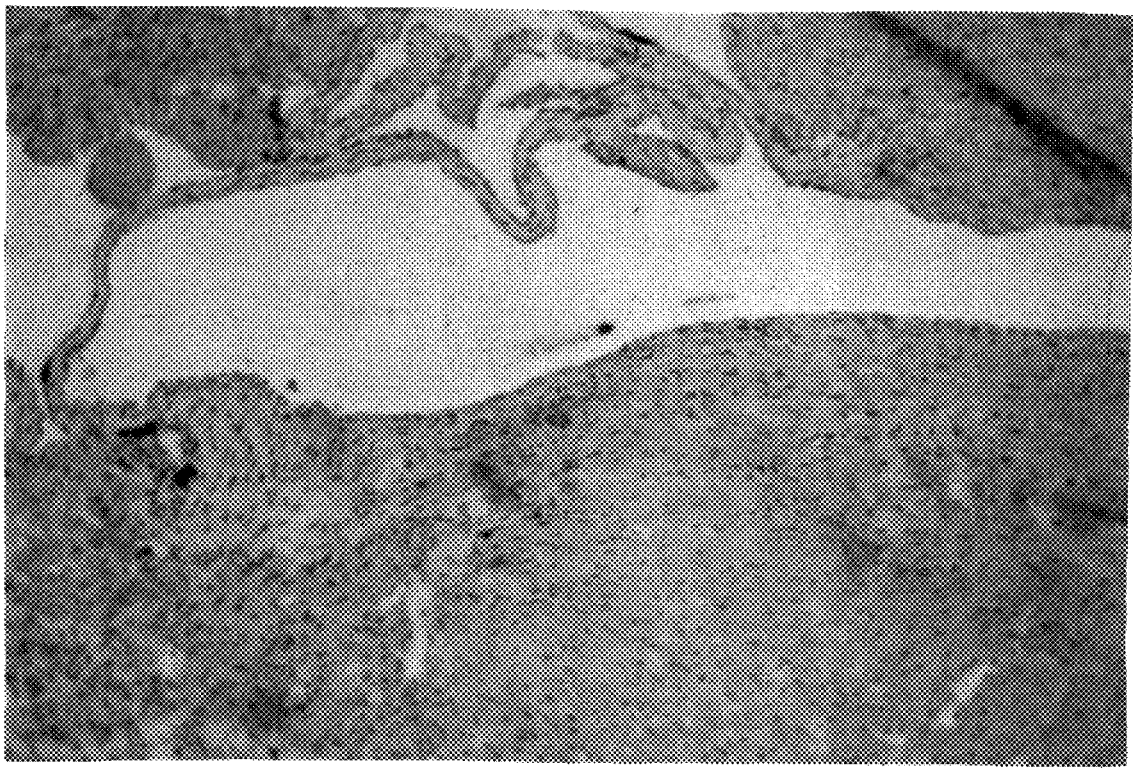
FIG. 1E shows the same as FIG. 1C except from another test animal.
Figure 1F:
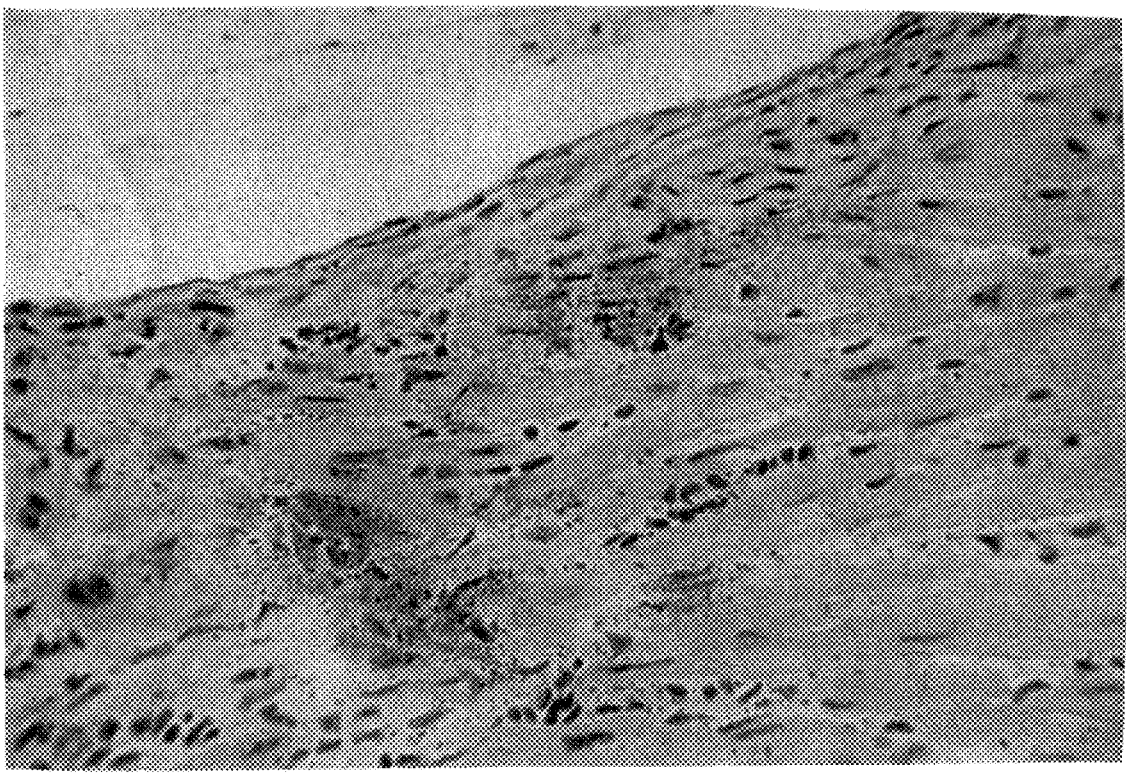
FIG. 1F shows an expanded view of the region shown in FIG. 1E.
Figure 2A:
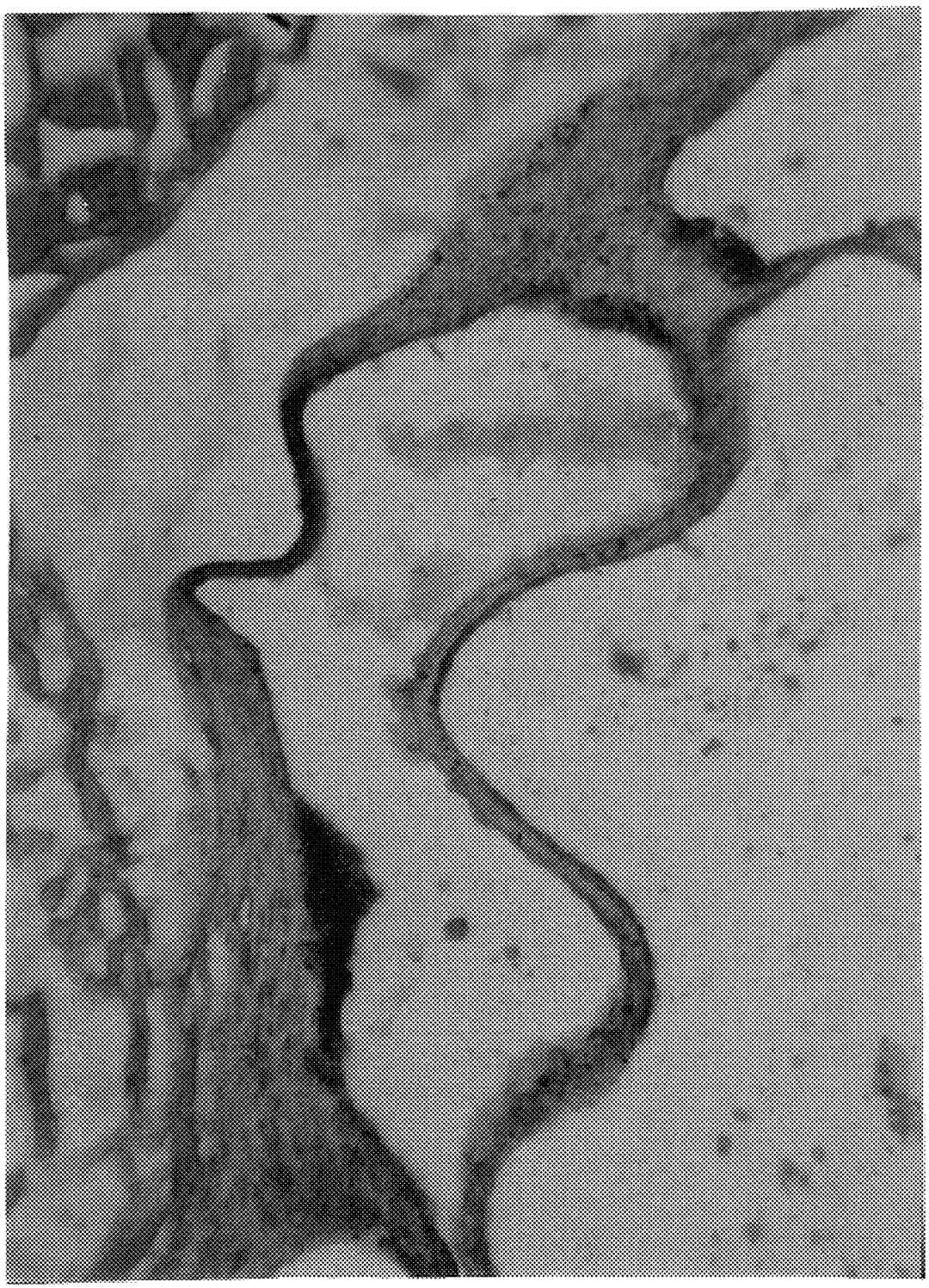
FIG. 2A shows minimal lesions in the aorta of the experimental animal.
Figure 2B:
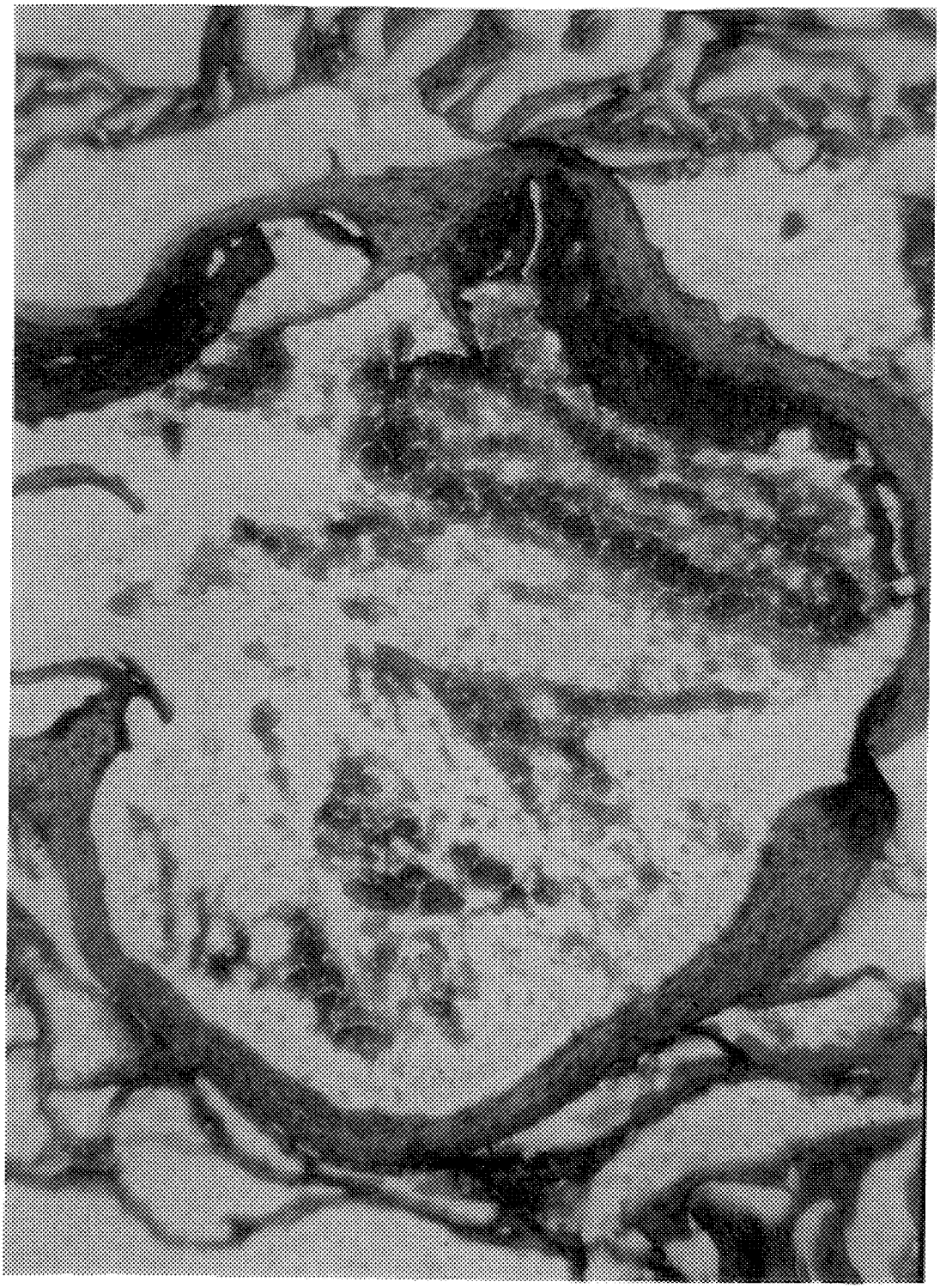
FIG. 2B shows fat accumulation in the aorta of the experimental animal.
Figure 2C:
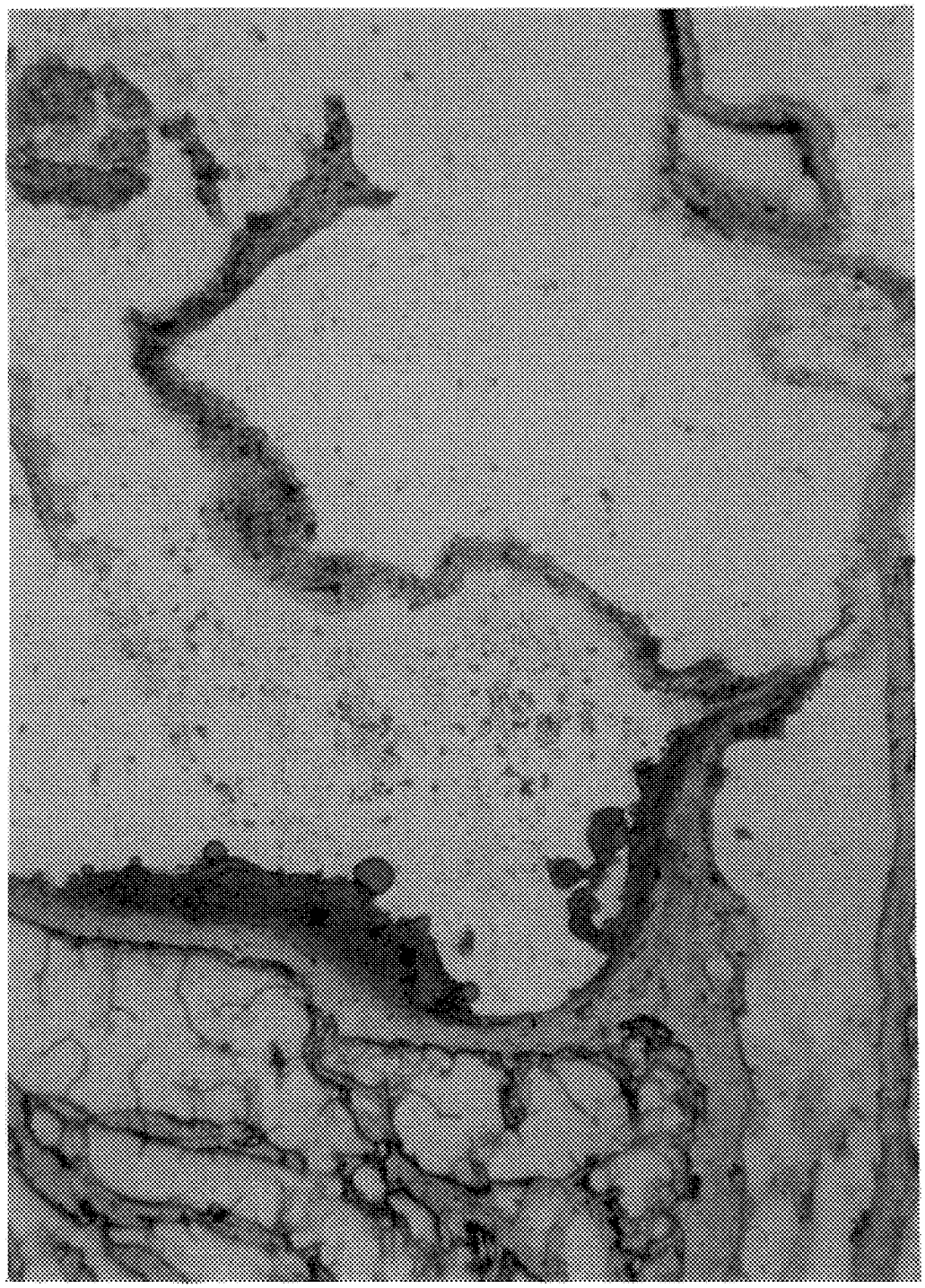
FIG. 2C shows fat accumulation in the aorta of the experimental animal.
Figure 2D:
FIG. 2D shows extensive lesions in the aorta of the experimental animal.
Figure 2E:
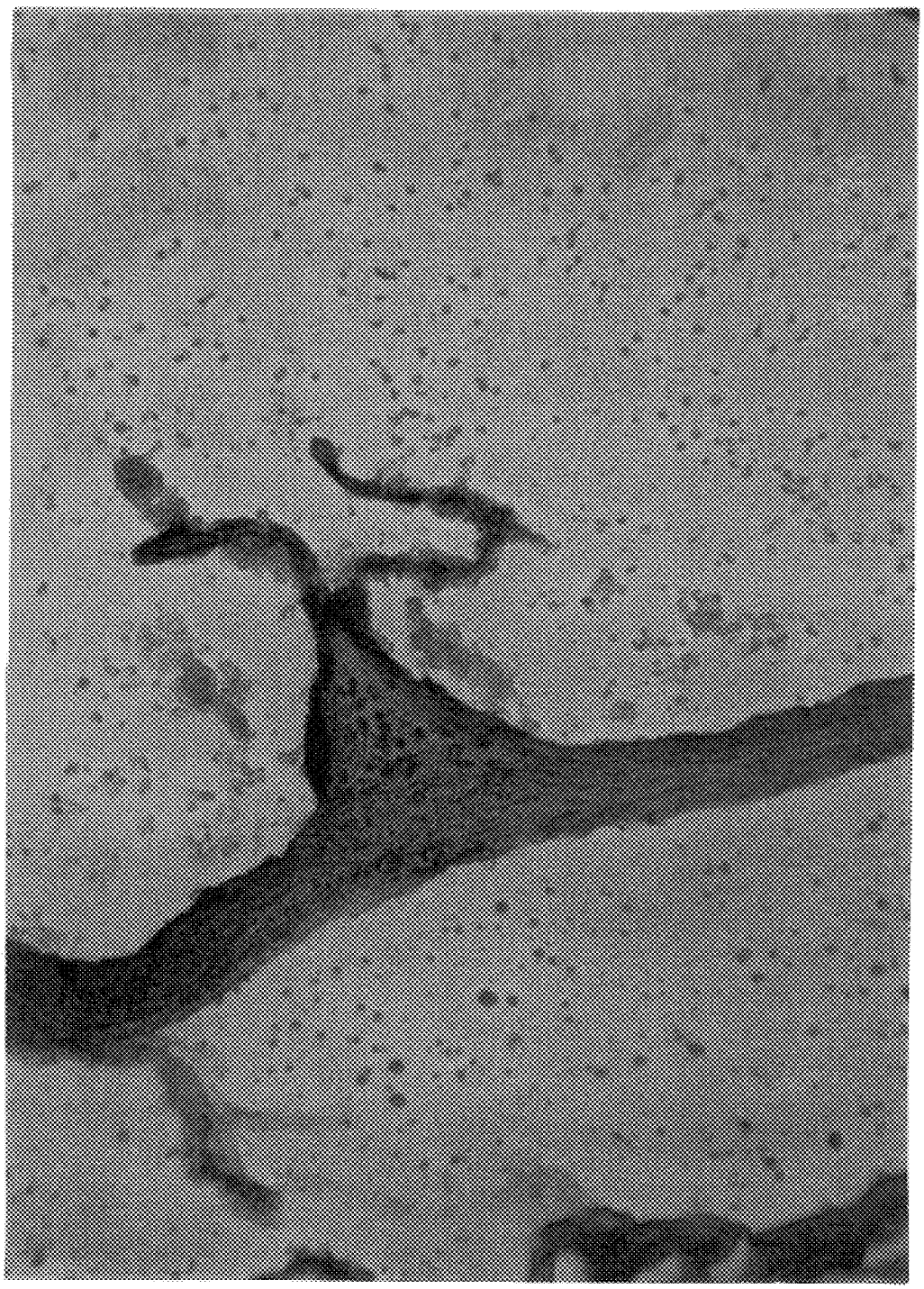
FIG. 2E shows minimal lipid accumulation in the aorta of the experimental animal.
Figure 2F:
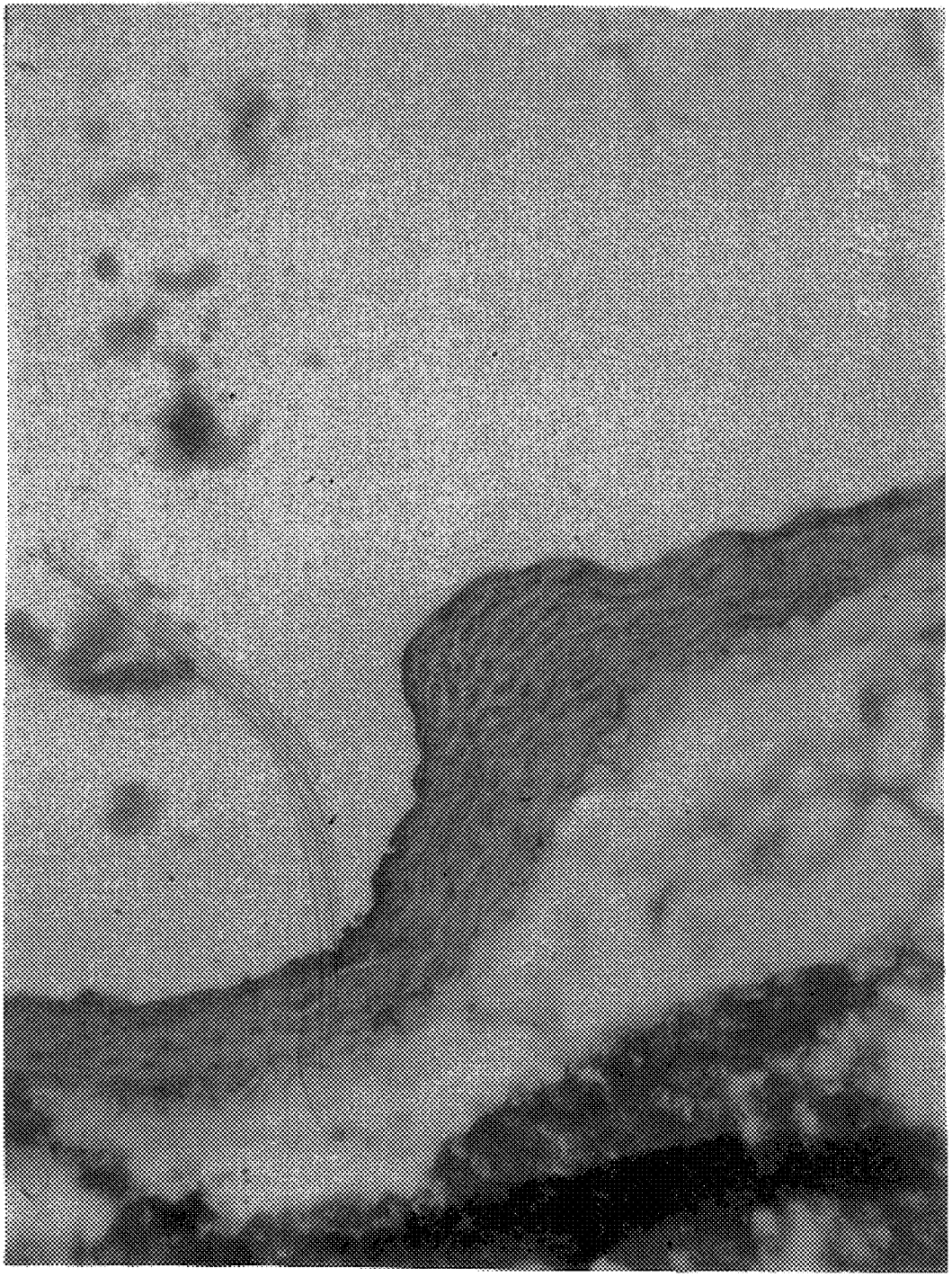
FIG. 2F shows no lesions in the aorta (maximum protection) of the experimental animal.
Figure 2G:
FIG. 2G shows minimal lesions in the aorta of the experimental animal.
Figure 2H:
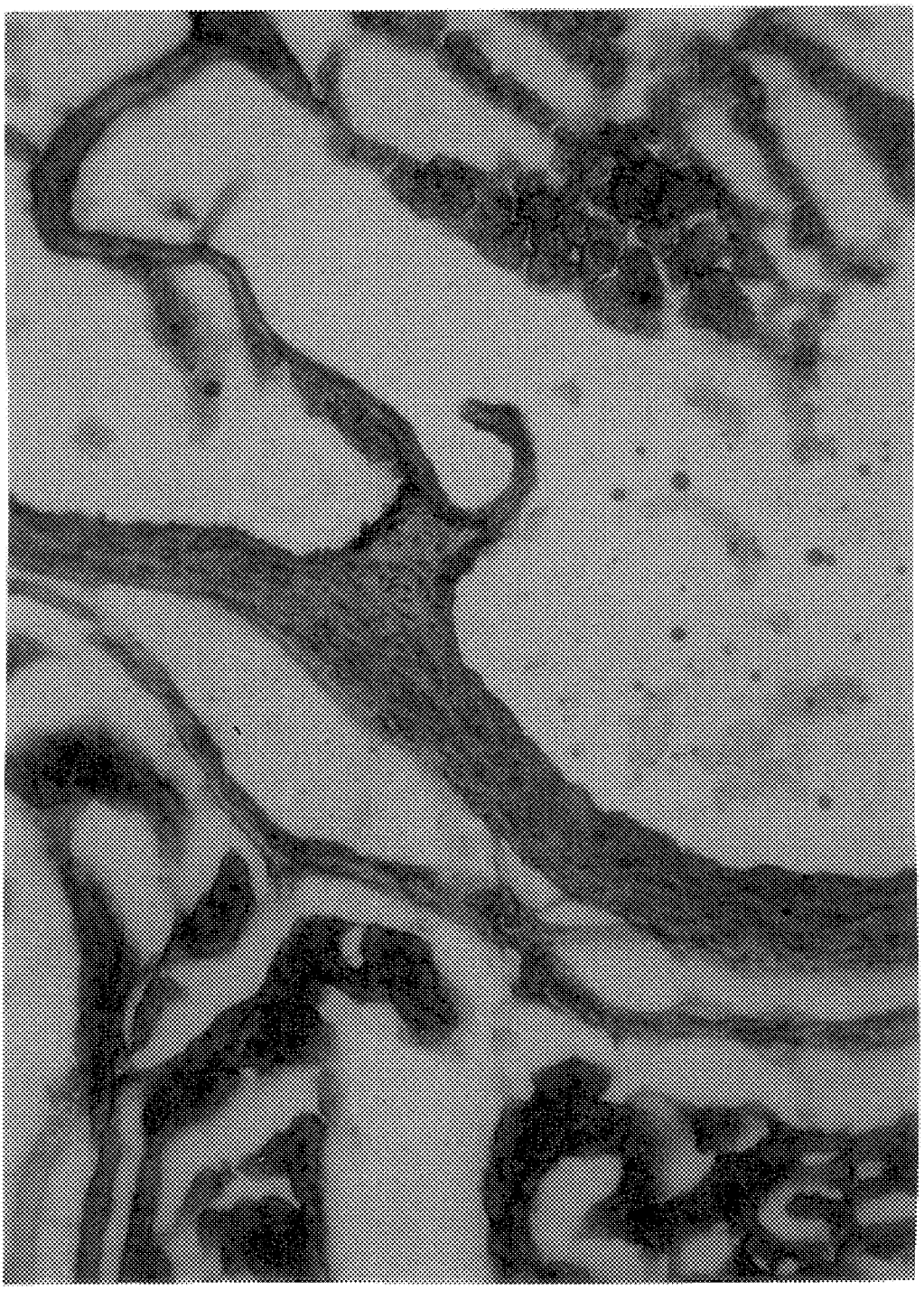
FIG. 2H shows practically no lesions in the aorta of the experimental animal.

The minimal structural features of human apoA-I (HDL) that inhibit and/or reverse atherosclerosis are disclosed herein. Based on the understanding that an amphipathic helical motif is the structural and functional domain in exchangeable apolipoproteins, the present invention indicates that peptide mimics of human apoA-I are capable of inhibiting diet-induced foam cell formation in mice. The present invention also discloses that peptide injection in ApoE knockout mice inhibits atherosclerosis.

The present invention is directed to a novel synthetic peptide having the sequence shown in SEQ No. 2 below. This peptide was effective in ApoE knockout mice.

The present invention is also directed to a pharmaceutical composition, comprising a novel synthetic peptide having the sequence shown in SEQ No. 2 below and a pharmaceutically acceptable carrier.

The present invention is also directed to a novel synthetic peptide having the sequence shown in SEQ No. 3 below.

The present invention is also directed to a pharmaceutical composition, comprising a novel synthetic peptide having the sequence shown in SEQ No. 3 below and a pharmaceutically acceptable carrier.

The present invention is also directed to a transgenic animal expressing one of the proteins shown in SEQ Nos. 1–3.

The present invention is also directed to a vector expressing one of the proteins shown in SEQ Nos. 1–3.

The present invention is also directed to a host cell transfected with a vector expressing one of the proteins shown in SEQ Nos. 1–3. Construction of vector and transfection of host cells in well known in this art and a person having ordinary skill in this art would be able to construct such vector and host cells readily for a variety of uses as would be apparent from the teachings of the instant specification.

The present invention is also directed to a method of treating atherosclerosis in an animal in need of such treatment comprising the step of administering to the animal a pharmacologically effective dose of a antiatherosclerotic peptide shown in SEQ Nos. 1–3.

It is specifically contemplated that pharmaceutical compositions may be prepared using the novel proteins of the present invention. In such a case, the pharmaceutical composition comprises the novel protein of the present invention and a pharmaceutically acceptable carrier. A person having ordinary skill in this art would readily be able to determine, without undue experimentation, the appropriate dosages and routes of administration of the novel proteins of the present invention.

The amphipathic helical motif of plasma exchangeable apolipoproteins represent the fundamental paradigm in understanding the structural and functional properties of exchangeable apolipoproteins. Studies of model amphipathic helical peptides and regions of exchangeable apolipoproteins have provided insight into the structural requirement of the amphipathic helix for lipid association and motifs responsible for many of the functions of apolipoproteins.

The present invention provides a class A amphipathic helical peptide (18A) that, when synthesized as a head-to-tail dimer with a proline incorporated 18A-Pro-18A, produced a peptide that closely marked many in vitro properties of human apoA-I. The peptide 18A-Pro-18A has the sequence:

```
SEQ.No.1: Asp-Trp-Leu-Lys-Ala-Phe-Tyr-Asp-Lys-Val-Ala-Glu-
              1               5                      10

Lys-Leu-Lys-Glu-Ala-Phe-Pro-Asp-Trp-Leu-Lys-Ala-Phe-Tyr-Asp-
              15                    20                      25

Lys-Val-Ala-Glu-Lys-Leu-Lys-Glu-Ala-Phe
              30                    35

SEQ No. 3: Asp-Glu-Pro-Asp-Trp-Leu-Lys-Ala-Phe-Tyr-Asp-Lys-
               1               5                      10

Val-Ala-Glu-Lys-Leu-Lys-Glu-Ala-Phe-Pro-Asp-Trp-Leu-Lys-Ala-
               15                    20                      25

Phe-Tyr-Asp-Lys-Val-Ala-Glu-Lys-Leu-Lys-Glu-Ala-Phe
               30                    35                      40
```

The following is a list of the properties of the amphipathic helical peptide (18A) compared with human apo A-I.

1. The tandem repeating class A amphipathic helix linked by a proline forms an optimal arrangement for lipid association.

2. The amphipathic helical peptide 18A-Pro-18A is the closest mimic of human apoA-I as a bilayer stabilizer. Bilayer stabilizers increase the transition temperature of DOPE whereas destabilizing molecules decrease the transition temperature. Such a destabilization can cause the inverted phase lipids (or hexagonal phase). Formation of this by the lytic peptide can be inhibited by human apoA-I or class A peptides. This explains the membrane stabilizing properties of human apoA-I. In these experiments, the amphipathic helical peptide 18A-Pro-18A showed most bilayer stabilizing property. Compared to 18A-Ala-18A and 18A-18A, 18A-Pro-18A also formed the most stable complex.

3). The amphipathic helical peptide 18A-Pro-18A is the most effective peptide in a) HIV-I Gp4l-induced cell fusion, b) neutrophil activation, c) BSA-induced lysis of fatty acid-containing vesicles and d) stimulating human placental lactogen synthesis. These properties are also exhibited by human apo A-I.

4) The amphipathic helical peptide 18A-Pro-18A mimics HDL in clearing cellular cholesterol. The removal of cholesterol from peripheral cells by HDL is thought to initiate the process of reverse cholesterol transport. HDL is capable of stimulating the net release of cholesterol from cells. This process thus inhibits the formation of foam cells, the hallmark of atherosclerosis. Similar to apo A-I and HDL, the amphipathic helical peptide 18A-Pro-18A effectively effluxes phospholipid and cellular cholesterol from cholesterol-loaded cells.

5) The amphipathic helical peptide 18A-Pro-18A competes with HDL for binding to rat adrenal cells. Recently, it has been shown that HDL delivers cholesterol to the cells through class B scavenger receptor SRBI. This receptor binds HDL with high affinity and is primarily expressed in the liver and in nonplacental steroidogenic tissues. The peptide 18A-Pro-18A competes with apo A-I and HDL for rat adrenal cells, indicating that the peptide binds to the HDL receptor.

6) In rats, in vitro turnover of human apo A-I and 18A-Pro-18A clearance curves are virtually superimposable.

The following examples are given for the purpose of illustrating various embodiments of the invention and are not meant to limit the present invention in any fashion.

EXAMPLE 1

IP administration of 18A-Pro-18A and apo A-I in mice

Since the peptide administration experiments involves intraperitoneal administration of peptide, the effect of administration of radiolabelled peptide and human apo A-I was compared in mice. Briefly, approximately 200,000 cpm of either the peptide (4.4 μg) or human apo A-I (3.0 μg) were administered intraperitoneally into 57BL6/J mice and blood samples were taken by retro-orbital bleeding from anesthetized animals. The final time point was taken from the axilla of anesthetized animals. Radioactivity was measured in plasma sample, and was calculated as total plasma cpm, assuming plasma volume as 4.2% of the body weight.

Total plasma cpm as a percent of the injected cpm reached 25.5% for 18A-Pro-18A and 32% for human apo A-I at 4 or 5 hours (respectively) after injection. Based on the specific activity of the radiolabelled materials, approximately 1 mg of the injected dosage was present in the blood after 4 or 5 hours following the injection. Full pressure liquid chromatographic (FPLC) analysis of the isolated lipoprotein fractions indicated the presence of the radiolabel exclusively in HDL in both the cases. It should be noted that the major lipoprotein in 57BL6/J mice is HDL.

EXAMPLE 2

Peptide 18A-P-18A administered to high fat diet C57BL 6/J Mice

C57BL mice were administered a high cholesterol diet (modified Thomas Hartcroft) and were divided into two groups. Group I received intraperitoneal administration of saline each day for 16 weeks. Group II received intraperitoneal administration of the peptide solution (μg/mice/day) for 16 weeks. At the end of the experiment, mice were sacrificed and aortas were harvested, cross-sectioned and stained with Oil Red O. FIGS. 1A–1F show the cross sections of the aortas from animals 1 and 2.

The results demonstrate that IP injection of both 18A-Pro-18A and human apo A-I resulted in similar amounts entering the plasma. Further, based on TCA precipitation and FPLC analysis, most of the radioactivity in the plasma at early time points (up to 5 hours) is present in the intact peptide/protein, thus indicating the peptide and human apoA-I are identical in their association with HDL. Thus, intraperitoneal administration allows for the peptide or human apoA-I to be released into plasma gradually. Intraperitoneal administration of the peptide is therefore feasible

EXAMPLE 3

IP administration of peptide in diet-administered 57BL6J mice

A dosage of peptide to be injected was selected based on the in vivo studies conducted using 18A to inhibit the LPS-induced toxicity in mice (Levine, et al., *PNAS,* 1993, 90:12040–12044). In these experiments, 80 mg of the peptide 18A was used per mouse to inhibit endotoxin-induced death of mice. Because of the solubility of the peptide 37pA, and since it was desirable to maintain the same volume used by Levine et al, 60 mg of peptide per mouse per day was injected.

Peptide 18A-Pro-18A dissolved in sterile saline was administered IP everyday for sixteen weeks 11 animals on high fat diet. Control animals on high fat diet were administered saline for sixteen weeks. At the end of sixteen weeks, animals were sacrificed and histology of hearts were done. The mortality in both the groups were similar (only three in each groups) indicating no toxicity due to peptide 18A-Pro-18A administration. Furthermore, no antibody was detected to the peptide. This is to be expected because peptide 18A-Pro-18A has been shown to interact with lipoproteins and circulates as a part of lipoproteins.

Regardless of the diet administered, aortal cross sections from control animals exhibited extensive lesions and formation of foam cells (FIG. 1A). In peptide 18A-Pro-18A administered animals, compared to the control group, less lipid accumulation was seen (FIG. 1C) indicating that the peptide has inhibited diet-induced lipid accumulation that is normally observed in C57 BL6/J mice. These results strongly demonstrate that peptide 18A-Pro-18A inhibits diet-induced lipid accumulations in these animals.

TABLE I

Effect of peptides on total cholesterol in high fat administered mice

| Animal | Total cholesterol (mg/dL)* |
|---|---|
| Control mice on normal diet | |
| Mouse-1 | 115 |
| Mouse-2 | 108 |
| Mouse-3 | 113 |

TABLE I-continued

Effect of peptides on total cholesterol in high fat administered mice

| Animal | Total cholesterol (mg/dL)* |
|---|---|
| Control mice on high fat diet and saline administered | |
| Mouse-1 | 297 |
| Mouse-2 | 320 |
| Mouse-3 | 232 |
| Mice on high fat diet and peptide administered | |
| Mouse-1 | 156 |
| Mouse-2 | 161 |
| Mouse-3 | 182 |

Similar experiments were completed in apoE-knockout animals. The peptide used was a modified 18A of the present invention with the sequence:
SEQ No. 2: Ac-Asp-Trp-Leu-Lys-Ala-Phe-Tyr-Asp-Lys-Val-Phe-Glu-Lys-Phe-Lys-Glu-Phe-Phe-$NH_2$.

This peptide was administered to animals on a normal diet, to determine if the intraperitoneal administration of this peptide would inhibit lesions that these animals produce spontaneously, even without high fat diet administration. The lesions in this case is different than that produced after sixteen weeks of high fat diet administration in 57BL6/J mice.

The results of the cholesterol profile after sixteen weeks indicate clearly, compared to control animals, that VLDL-density particles have decreased considerably in peptide-administered animals. More importantly, histological examination of aortal cross section from control mice shows classical lesion that is typical for the apoE-knockout mice.

FIGS. 2A–2H show that the intraperitoneal administration of the modified 18A peptide to apoE-knockout mice has virtually no lesion. While the mechanism of this inhibition is not clear, cholesterol profiles indicate that the peptide is changing the VLDL-like cholesterol rich particles, perhaps by acting as a lipoprotein lipase activator. This is indicated by the IDL type particles that are formed in the cholesterol profile. The LDL formed may then be cleared by the LDL receptor pathway. Since the in vitro results show that the peptides are effective effluxers of cellular cholesterol, it is also possible that the peptides are inhibiting the occlusion of cholesterol on the endothelial layer.

EXAMPLE 4

Peptide-expressing transgenes and expression in mammalian cells

The antiatherogenicity of human apoA-I has been studied in mice by producing human apoA-I transgenes. In a similar manner, peptide transgenics were produced to illustrate the antiatherosclerotic properties of the expressed peptides in mice on high fat diets. Briefly, the peptide transgenes were produced using the following protocol.

Since both mouse and human apo A-I start with the same first three amino acids, Asp-Glu-Pro, the first three amino acids of the secreted peptide had these amino acids. Thus, the targeted peptide was Asp-Glu-Pro-18A-Pro-18A. The biosynthesis of apo A-I will have a pro sequence and preprosequence as its precurssor. The human pro and prepro sequence was therefore included in the nucleotide sequence of the peptide to produce the peptide gene. Thus, the following nucleotides were used as templates and primers.

Figure 3A:
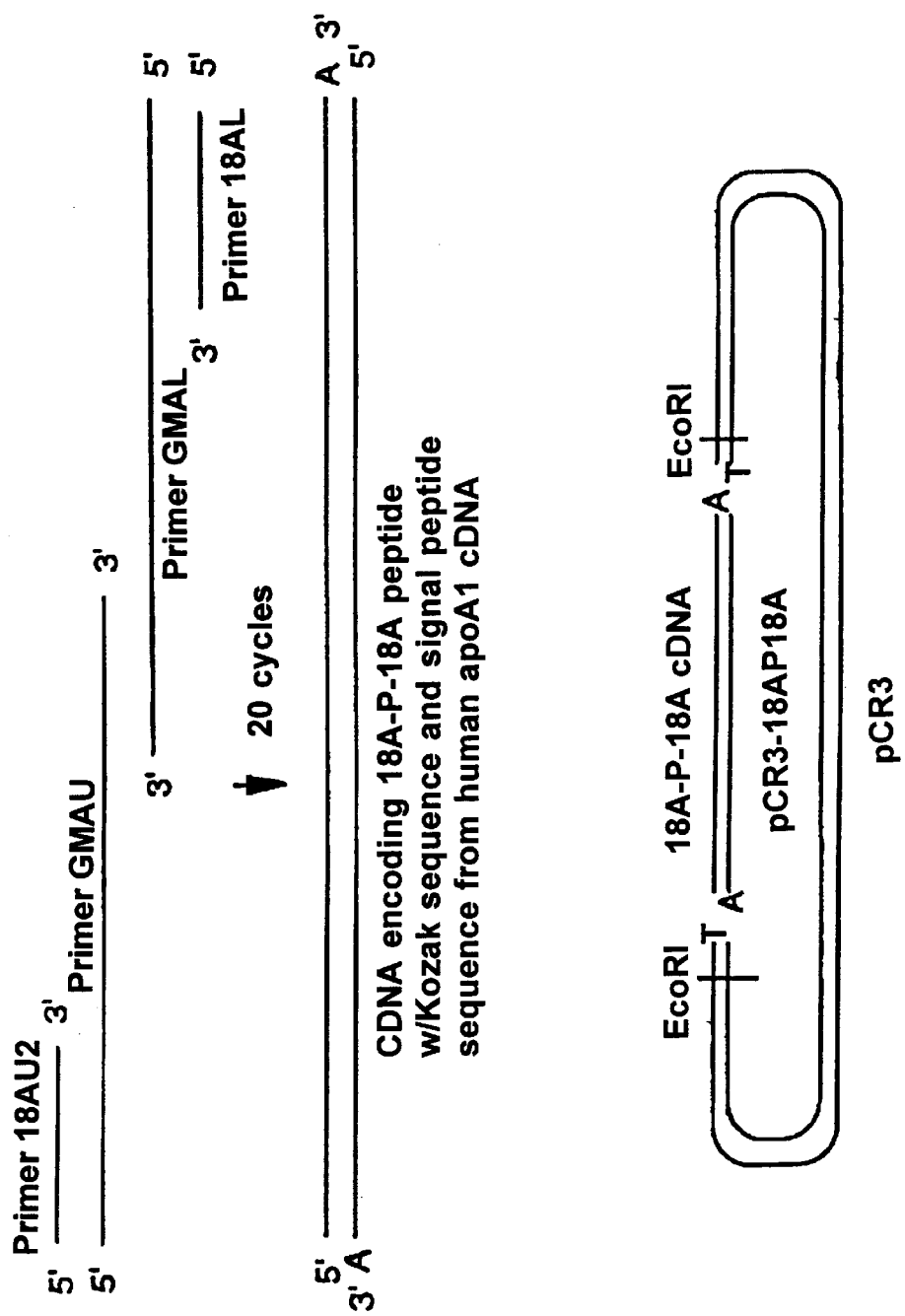
FIGS. 3A and 3B show a detailed schematic illustrating the construction of the amphipathic peptide gene.
Figure 3B:
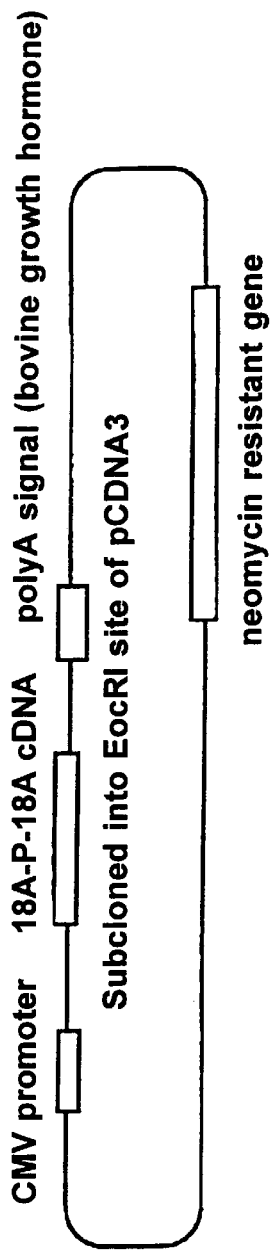
Figure 3B:
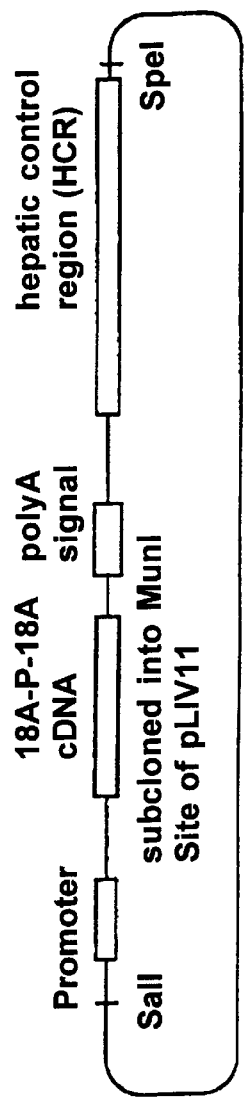
Figure 4:
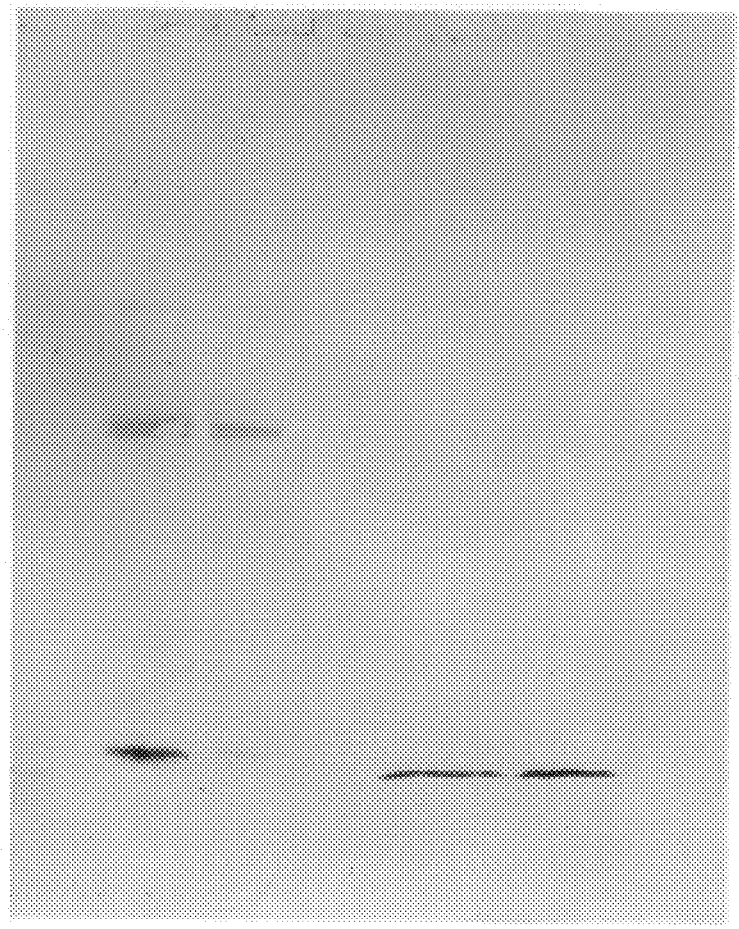
FIG. 4 shows a gel showing a Western analysis using the polyclonal anitbody specific for peptides of the present invention. lanes 1 to 4, respectively: 1) McArdal cells transfected with the peptide gene; 2) Control cells; 3) Peptide 18A-Pro-18A; and 4) Asp-(Glu-Pro-18A-Pro-18A.

FIGS. 3A and 3B show the contruction of the amphipathic peptide gene. The primers are designed to be able to ligate the PCR product onto PCR 3 vector using the TA cloning kit. The primers are designed so that the PCR product would have a complementary overhang that would complement the overhang in the vector produced by the EcoRI treatment of the PCR 3 vector. Thus the PCR product was subcloned into PCR3 vector by TA cloning. After propagation and sequencing of the inserted sequence to confirm sequencing and direction of ligation, the peptide gene was cut out using EcoRI and subcloned into PCDNA3 for stable transfection. McArdal cells were transfected with the above. After culturing cells, the cells were boiled with SDS and the mixture was run on an SDS-PAGE (8–25%) and Western blotted with the antibody specific for the peptide. A control peptide was also run. The cells transfected with the peptide gene showed positive for antibody whereas the control cells were negative (FIG. 4). Thus, the authenticity of peptide gene was confirmed.

The peptide gene was then cloned into the MunI site of the apoE-promoter that is specific for expression of the peptide/protein in the liver. SalI-SpeI fragment of the apoE promoter to which the peptide gene was subcloned was microinjected into mouse oocytes to produce transgenic mice. Only 2 out of 32 mice showed positive to the inserted gene by southern analysis using apoE promoter as the probe. Further transgenic mice were generated from these two founders and analysed for the presence of peptide gene.

To obtain more animals, semen from one male mouse that possessed peptide gene was harvested and mice were produced by an in vitro fertilization (IVF) method. This produced a number of animals with the peptide gene present in different amounts. Western analysis using the antibody produced for the chemically synthesized peptide indicated the presence of peptide in different amounts (FIG. 4). Some of the mice possessed very little peptide, and some possessed considerable amount of peptide in the plasma (approximately 20 μg/ml of the plasma obtained by the retroorbital bleed of the animals).

The animals were then administered TeckLad diet that is known to produce foam cell lesions in 57BL6/J mice when administered for sixteen weeks. At the end of sixteenth week, mice were sacrificed, plasma was collected and the hearts were harvested. The aortal cross-sections were stained with Oil Red O that stains lipid laden fatty streaks. The plasma samples were subjected to lipoprotein analysis. The results of plasma analysis indicated clearly that the profiles were different from each other and some of the profiles looked very similar to the control mice on the normal diet, with the cholesterol values around ≦100 mg/dl. Thus, the present invention demonstrates clearly that the peptides disclosed herein are capable of inhibiting the production of atherogenic lipoproteins. These mice also had a profile in which the HDL was similar to the normal mice. Some mice possessed high levels of VLDL density lipoproteins.

EXAMPLE 5

Construction of amphipathic helical peptide gene

The construction of amphipathic helical peptide gene was as follows.

```
Upper Primer: Length 26
TT CAG GATG AAA GCA GCG GTG TTA AC                          (SEQ. No. 4)

Lower Primer: Length 20
TCA GAA TGC TTC TTT TAG TT                                  (SEQ. No. 5)

Upper Template: Length:108 residues
ATG AAA GCA GCG GTG TAA ACA CTA GCA GTA CTC TTC CTG ACG GGG
 M   K   A   A   V   L   T   L   A   V   L   F   L   T   G
I<              Pre                                       >I AGT CAA GCT CGG CAT TTC TGG CAG CAA GAT GAA CCC GAC TGG CTG
 S   Q   A   R   H   F   W   Q   Q   D   E   P   D   W   L
         Prepro             >I I<first 3 of A-I>I I<start of 37pA AAG G CG TT C TAC GAC AAG                                   (SEQ. No. 6)
 K   A   F   Y   D   V                                      (SEQ. No. 7)

Lower Template: Length-108 residues
GAC TTC CGC AAG ATG CTG TTC CAC CGC CTC TTC GAC TTC CTC CGC
 L   K   A   F   Y   D   K   V   A   E   K   L   K   E   A
                        37pA continued AAG GGG CTA ACC AAT TTT CGT AAA ATA CTA TTT CAT CGT CTT TTT GAT
 F   P   D   W   L   K   A   F   Y   D   K   V   A   E   K   L
                        37pA continued TTT CTT CGT AAG ACT                                         (SEQ. No. 8)
 K   E   A   F  Stop codon                                  (SEQ. No. 9)
    end of 37pA >I
```

EXAMPLE 6
McArdal Cells Transfected with PCDNA3 Containing the Peptide Gene

The gel shows Western analysis using the polyclonal antibody specific for peptide. As positive controls, peptide Asp-Glu-Pro-18A-Pro-18A and 18A-Pro-18A were used. As a negative control, control cells were used. The peptide gene transfected cells and control cells were heated for 5 minutes with 1% SDS and loaded on an 8–25% gel and run under denaturing conditions. The proteins were transferred onto the cellulose membrane and Western blotted with the polyclonal antibody raised in rabbits against the synthetic peptide Asp-Glu-Pro-18A-Pro-18A.

The cells transfected with the peptide gene showed positive to the peptide antibody, the size indicated to be similar to bands due to the synthetic peptides 18A-Pro-18A and Asp-Glu-Pro-18A-Pro-18A. (FIG. 4)

EXAMPLE 7
Southern analysis of tails from peptide transgenes

Figure 5:
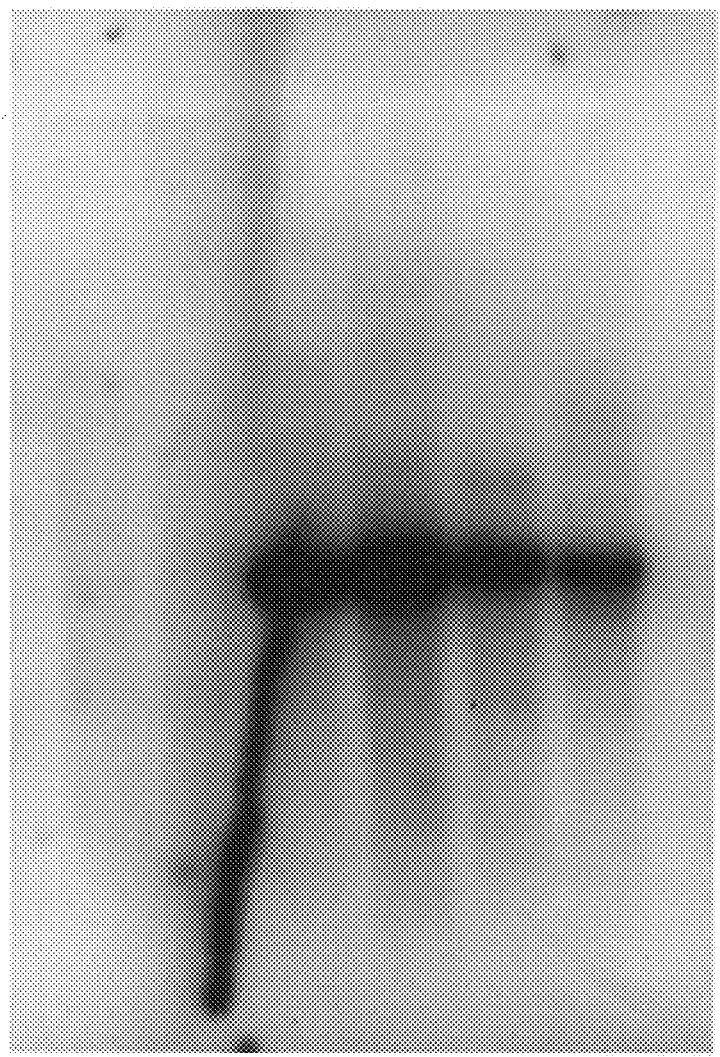
FIG. 5 shows a Southern analysis of tails from peptide transgenes. The numbers 1–6 refer to Southern analysis of plasma in different experimental animals.

Southern analysis was done on a piece of the mice tails using a radiolabelled pLiv 11 vector that is a liver specific apoE promoter, used for incorporating the peptide gene. Two animals were negative as shown in the gel and four animals were positive for the incorporated gene, indicating the presence of peptide gene in these mice (FIG. 5).

Figure 6:
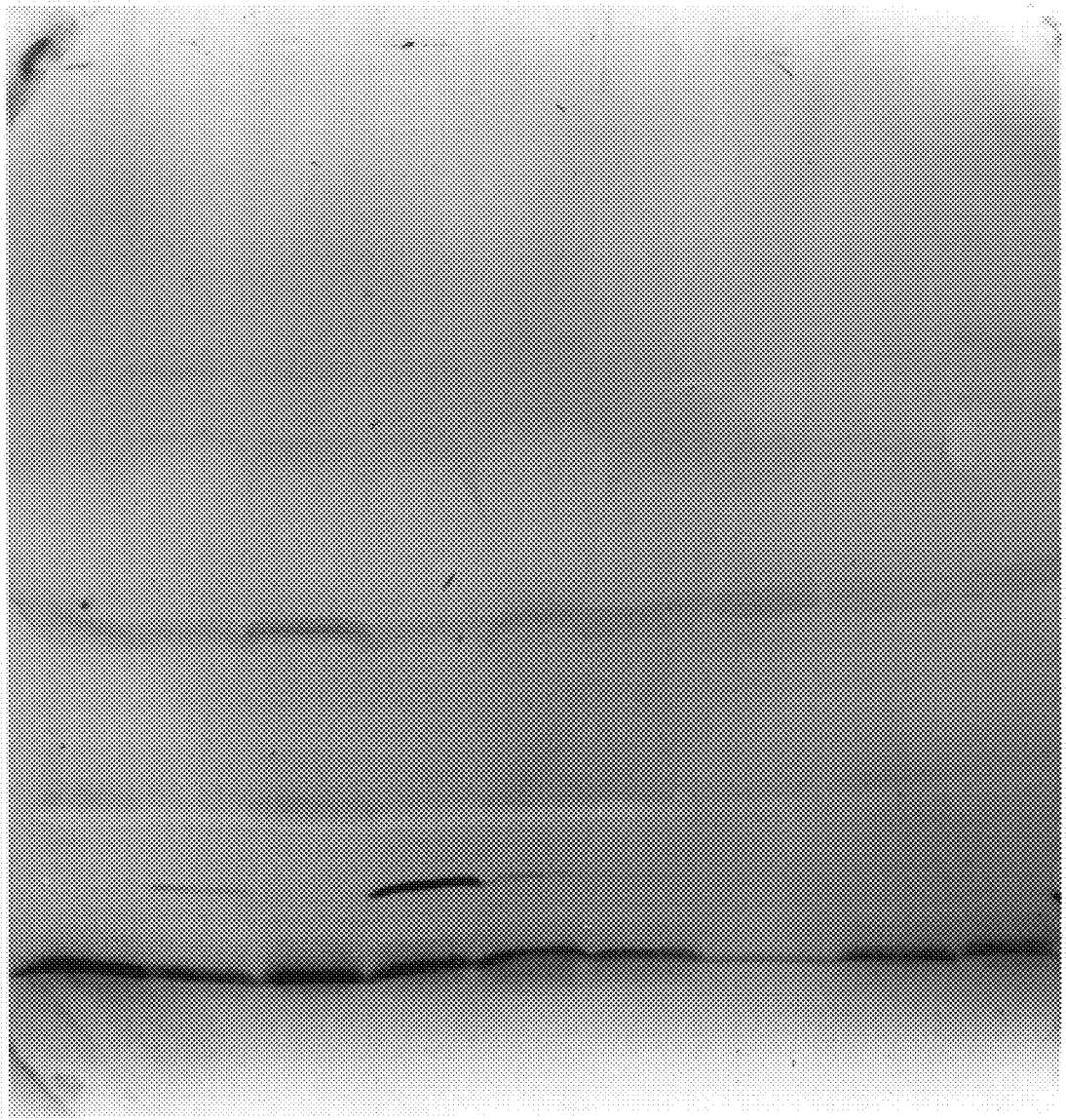
FIG. 6 shows a representative western analysis of plasma from nine in vitro fertilized transgenic mice using the polyclonal antibody specific for the synthetic peptide of the present invention.

EXAMPLE 8
Western analysis of plasma from in vitro fertilized transgenic mice using the polyclonal antibody specific for the synthetic peptide Blood from the in vitro fertilized animals were obtained from the retroorbital bleed and red cells were separated by centrifugation. The plasma samples were treated with 1% SDS and subjected to SDS-PAGE as described before. After transferring to the nitrocellulose membrane, the membrane was subjected to Western analysis using the polyclonal antibody produced in rabbit against the synthetic peptide Asp-Glu-Pro-18A-Pro-18A. The plasma from different mice reacted with the peptide antibody (indicating the presence of circulating peptide in plasma), and the gel also indicated that the amount of peptide circulating in the plasma was different in different animals. Thus, if the observed protective effect towards high fat diet is due to the circulating peptide, then the severity of lesion observed in different animals would be different (FIG. 6).

EXAMPLE 9
Aortal Cross Sections from IVF Animals Show Lesions of Different Severity In vitro fertilized animals were subjected to Southern analysis and some of them were found to possess the peptide gene. Those animals that possessed the peptide gene were also positive to polyclonal antibody, indicating the presence of the peptide in circulating plasma. These animals were administered high fat diet and after 16 weeks, the hearts were isolated, the aortal cross sections were subjected to Oil Red O stain.

As can be seen in FIG. 2, the extent of lesions (as indicated either by the red lipid droplets, or black spots due to lipid filled macrophages) varied from severe to very mild accumulation of the lipid in the aorta of these animals. These results are in agreement with the plasma cholesterol profiles.

EXAMPLE 10
Plasma cholesterol profiles of IVF transgenic mice that were administered with high fat diet for sixteen weeks The plasma cholesterol profiles were obtained by the vertical autoprofile (VAP), a method exclusively developed to analyze small amounts of plasma samples. As can be seen from the profiles, the control animals possess high levels of HDL and very low levels of LDL and VLDL. The total cholesterol is $\leq 100$ mg/dl. Mice fed with high fat diet had cholesterol profiles showing high levels of plasma cholesterol ($\geq 220$ mg/dl). The profile also shows less of HDL and more of VLDL density lipoproteins.

In transgenic mice fed with high fat diet, the cholesterol profiles varied from being close to the normal mice to similar to the ones with control mice fed with high fat diet. The normal cholesterol profile is a clear indication of the fact that the peptide transgenes have less lipid accumulation. This is confirmed by the cross-sectional analysis of aorta from these mice after sixteen weeks of high fat diet administration. Thus, the peptide not only by IP administration, but also when synthesized by the animals by the microinjection of the peptide gene, protected mice from diet administered atherosclerosis.

EXAMPLE 11
Atherosclerosis protection by model amphipathic helical peptides

Atherosclerosis protection by model amphipathic helical peptides is shown in fat-sensitive mice by intraperitoneal injection or transgenic overexpression. Plasma lipoprotein cholesterol profiles are characterized in the diet administered. Histological evaluation of the effect of well characterized amphipathic peptides with well defined properties on the extent of atherosclerosis is shown. The ability of peptide to stabilize or regress atherosclerotic lesions is determined.

Atherosclerosis protection by model amphipathic helical peptides is shown in apoE-knockout mice which spontaneously develop atherosclerotic lesions. Peptide intraperitoneal administration or expression of peptide transgenes mice lacking apoE gene shows the ability to inhibit lesions. Site of and expression of peptide is correlated to the severity of lesions.

EXAMPLE 12
Site-directed mutants of human apolipoprotein A-I

Site-directed mutants of human apolipoprotein A-I are expressed in mammalian cells as intact lipoprotein with functional studies of mutant apoA-I particles (HDL subspeciation, LCAT activation, interaction with putative HDL receptor). Further, a well characterized apoA-I mutant is overexpressed in transgenic mouse models to determine the degree of atherosclerosis protection either towards high fat diet-induced atherosclerosis or in apo E knockout animals.

The correlation between HDL and apoA-I can be shown by computer modeling, peptide studies of human apo A-I sequence and site-directed mutagenesis studies. Thus, it is possible to understand the structure-function of lipoproteins and the mechanisms of antiatherosclerotic properties of HDL. The modeling studies have also been useful to understand the structure of apo B, the protein component of LDL, the lipoprotein whose levels are directly correlated to the incidence of atherosclerosis.

In apo E-knockout mice, increased levels of VLDL-density lipoprotein, that is not TG-rich, is present (see above). This is the reason that apo E-knockout mice develop atherosclerosis and expression of human apo A-I in these animals inhibits atherosclerosis. In contrast, Apo C-II is involved in the activation of LPL. Increased LPL activity has been shown to inhibit atherosclerosis in apo B-receptor knockout mice that are fed a high fat diet (Shimada, et al., Proc. Natl. Acad. Sci. 93:7242–7246 (1996)).

EXAMPLE 13
Synthetic Peptide Analogs of the Amphipathic helix

The amphipathic helix is a structural and functional motif not only in apolipoproteins, including apo B, but also in many other biologically active peptides and proteins. Peptide analogs can be designed to mimic many of the properties of exchangeable apolipoproteins. More importantly, the peptides can mimic the properties of apoA-I in vitro and in some cases, can also act as stimulators of LPL. Many of the peptides are nontoxic and do not produce antibodies. It is also possible to design peptides with a selective function. Thus, one can examine the effect of a particular property of a particular peptide (or particular property of exchangeable apolipoproteins) and their effect on the atherosclerosis.

TABLE II shows the correlation of plasma cholesterol values with the presence or absence of the synthetic peptide of the present invention and analysis of aortic cross-section. The peptide was demonstrated in animals 5, 7, 8, 16 and 68. Further, total cholesterol and minimal aortic lesions were seen in these animals.

TABLE II

Correlation of plasma cholesterol values with the presence or absence of peptide (SEQ ID No. 3) and analysis of aortic cross-section

| Animal number | Presence of peptide* | Total Cholesterol (mg/dL)** | Aortic lesion score*** |
|---|---|---|---|
| 5 | + | 188 | 2 |
| 6 | − | 231 | 3 |
| 7 | + | 166 | 1 |
| 8 | + | 178 | 1 |
| 9 | − | 377 | 3 |
| 13 | − | 297 | 3.2 |
| 15 | − | 240 | 1.6 |
| 16 | + | 190 | — |
| 68 | + | 181 | 1 |

*Presence of peptide was determined by Western analysis.
**Plasma cholesterol levels were determined after atherogenic diet administration for 16 weeks, at the time of sacrifice.
***Aortic lesion score was determined with 1 being minimal and 4 being extensive lesions.

TABLE III

Effect of peptides on total cholesterol
1. High fat diet administered to B16/SJL mice

| Animal No. | Diet | Peptide | Total cholesterol |
|---|---|---|---|
| Mouse 1 | normal | | 115 |
| Mouse 2 | | | 108 |
| Mouse 3 | | | 113 |
| Mouse 1 | High fat | | 297 |
| Mouse 2 | | | 320 |
| Mouse 3 | | | 232 |
| Mouse 1 | High fat | 5F | 156 |
| Mouse 2 | | 5F | 161 |
| Mouse 3 | | 5F | 182 |

5F: is the modified 18A peptide (SEQ ID No 2).

The results shown in TABLE III demonstrate that the modified 18A peptide injection markedly decreases the levels of plasma cholesterol. Peptide injections (50 μg/animal/day for 16 weeks).

Thus, as described in detail above, the present invention provides an anti-atherosclerotic peptide, the peptide being an amphipathic helical peptide compared with human apoA-I, characterized by having at least 4 of the following 8 properties: a tandem repeating class A amphipathic helix linked by a proline which forms an optimal arrangement for lipid association, has bilayer membrane stabilizing properties, inhibits HIV-I Gp41-induced cell fusion, inhibits neutrophil activation, inhibits bovine serum albumin-induced lysis of fatty acid-containing vesicles, stimulates human placental lactogen synthesis, effluxes phospholipid and cellular cholesterol from cholesterol-loaded cells, and competes with HDL for binding to cells. In one embodiment, the synthetic peptide has the sequence shown in SEQ No. 1 or fragments or derivatives thereof. In another embodiment, the synthetic peptide has the sequence shown in SEQ No. 2 or fragments or derivatives thereof. In yet another embodiment, the synthetic peptide has the sequence shown in SEQ No. 3 or fragments or derivatives thereof.

The present invention also provides a pharmaceutical composition, comprising a peptide disclosed herein and a pharmaceutically acceptable carrier. As is now well known in the art, a person having ordinary skill could create transgenic animals expressing the peptides disclosed herein. For various reasons, one may also create a vector expressing a peptide disclosed herein and a host cell transfected with such a vector.

The present invention also provides a method of treating atherosclerosis in an animal in need of such treatment, comprising the step of: administering to the animal a pharmacologically effective dose of a pharmaceutical composition disclosed herein.

The present invention also provides a class A amphipathic helical peptide, said peptide synthesized as a head-to-tail dimer with a proline incorporated therein, wherein the peptide mimicks the properties of human apoA-I.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An anti-atherosclerotic synthetic peptide, said peptide being an amphipathic helical peptide compared with human apoA-I, characterized by having at least 4 of the following 8 properties: a tandem repeating class A amphipathic helix linked by a proline which forms an optimal arrangement for lipid association, has lipid bilayer membrane stabilizing properties, inhibits HIV-I GP41-induced cell fusion, inhibits neutrophil activation, inhibits bovine serum albumin-induced lysis of fatty acid-containing vesicles, stimulates human placental lactogen synthesis, effluxes phospholipid and cellular cholesterol from cholesterol-laced cells, and competes with HDL for binding to cells; wherein said peptide has the sequence shown in SEQ ID NO. 3.

2. A pharmaceutical composition, comprising a peptide of claim 1 and a pharmaceutically acceptable carrier.

3. A method of treating atherosclerosis in an animal in need of such treatment, comprising the step of:

administering to the animal a pharmacologically effective dose of the pharmaceutical composition of claim 2.

4. A class A amphipathic helical peptide, said peptide synthesized as a head-to-tail dimer with a proline incorporated therein, wherein said peptide mimicks the properties of human apoA-I, and wherein said peptide has the sequence shown in SEQ ID NO. 3.

* * * * *